(12) United States Patent
Early et al.

(10) Patent No.: US 11,597,691 B2
(45) Date of Patent: Mar. 7, 2023

(54) PROCESS FOR SYNTHESISING METHANOL

(71) Applicant: JOHNSON MATTHEY DAVY TECHNOLOGY LIMITED, London (GB)

(72) Inventors: Simon Robert Early, London (GB); David McGregor Turnbull, Malborough (NZ)

(73) Assignee: Johnson Matthey Davy Technologies Limited, London (GB)

( * ) Notice: Subject to any disclaimer, the term of this patent is extended or adjusted under 35 U.S.C. 154(b) by 210 days.

(21) Appl. No.: 17/053,420

(22) PCT Filed: Apr. 16, 2019

(86) PCT No.: PCT/GB2019/051075
§ 371 (c)(1),
(2) Date: Nov. 6, 2020

(87) PCT Pub. No.: WO2019/220073
PCT Pub. Date: Nov. 21, 2019

(65) Prior Publication Data
US 2021/0371362 A1  Dec. 2, 2021

(30) Foreign Application Priority Data

May 17, 2018  (GB) .................................. 1808019.2

(51) Int. Cl.
*C07C 29/151* (2006.01)
*C07C 29/74* (2006.01)
(Continued)

(52) U.S. Cl.
CPC ............ *C07C 29/151* (2013.01); *C07C 29/74* (2013.01); *C07C 29/76* (2013.01); *C07C 31/04* (2013.01); *C07C 2523/72* (2013.01)

(58) Field of Classification Search
None
See application file for complete search history.

(56) References Cited

U.S. PATENT DOCUMENTS

| 4,226,795 A | 10/1980 | Bowman |
| 4,460,378 A * | 7/1984 | Di Pietro .............. C07C 29/153 518/704 |
| 6,846,951 B1 | 1/2005 | Thiebaut |

FOREIGN PATENT DOCUMENTS

| EP | 1 226 103 B1 | 4/2006 |
| WO | 2001032594 A1 | 5/2001 |

(Continued)

*Primary Examiner* — Medhanit W Bahta
(74) *Attorney, Agent, or Firm* — BakerHostetler

(57) ABSTRACT

A process for synthesising methanol is described comprising the steps of (i) passing a feed gas comprising a make-up gas containing hydrogen and carbon dioxide to a methanol synthesis loop, (ii) recovering a product gas mixture containing methanol from the methanol synthesis loop, (iii) cooling the product gas mixture to below the dew point to condense crude methanol, (iv) separating the crude methanol from an unreacted gas mixture, (v) passing a portion of the unreacted gas mixture to the methanol synthesis loop and (vi) recovering a portion of the unreacted gas mixture as a purge gas stream, characterised by contacting the crude methanol and a portion of the purge gas in a stripping unit to strip dissolved gases from the crude methanol thereby forming a stripped crude methanol and an enriched gas mixture, and feeding at least a portion of the enriched gas mixture to the methanol synthesis loop.

13 Claims, 2 Drawing Sheets

(51) Int. Cl.
*C07C 29/76* (2006.01)
*C07C 31/04* (2006.01)

(56) References Cited

FOREIGN PATENT DOCUMENTS

| WO | WO2013/144041 A1 | 10/2013 |
| WO | WO2016/180812 A1 | 11/2016 |

* cited by examiner

PROCESS FOR SYNTHESISING METHANOL

This invention relates to a process for synthesising methanol.

Methanol synthesis is generally performed by passing a synthesis gas comprising hydrogen and carbon monoxide and/or carbon dioxide at an elevated temperature and pressure through one or more beds of a methanol synthesis catalyst, which is often a copper-containing composition, in a synthesis reactor. A crude methanol is generally recovered by cooling the product gas stream to below the dew point and separating off the product as a liquid. The crude methanol is typically purified by distillation. The process is often operated in a loop: thus unreacted gas may be recycled to the synthesis reactor as part of the feed gas via a circulator. Fresh synthesis gas, termed make-up gas, is added to the recycled unreacted gas to form the feed gas stream. A purge stream is often taken from the circulating gas stream to avoid the build-up of inert gasses in the loop.

The crude methanol generally contains dissolved gases, including carbon dioxide, that are separated as part of the purification.

WO2013/144041 discloses a process for the preparation of methanol by (i) feeding a feed comprising carbon dioxide; and at least part of a first recycle gas stream comprising carbon dioxide and hydrogen, to a reactor, to obtain a gaseous feed with a hydrogen:carbon dioxide molar ratio of between 2-18:1; (ii) contacting the gaseous feed with a catalyst at a temperature of between 200 and 300° C. and a pressure of between 40 and 200 bar, thereby forming an outlet stream comprising methanol, water, carbon monoxide, carbon dioxide, and hydrogen; (iii) cooling the outlet stream; (iv) subjecting said outlet stream to a separation step, while optionally at least part of a second recycle gas stream is added to said outlet stream comprising methanol prior to and/or during said separation step, in which separation step methanol and water are separated from non-condensable components, thereby forming a methanol-comprising product stream and a first recycle gas stream; (v) stripping the methanol-comprising product stream using a hydrogen stream, thereby forming a purified methanol product stream and a second recycle gas stream; and (vi) feeding at least part of the first recycle gas stream to step (i) and at least part of the second recycle gas stream to steps (i) and/or (iv). The hydrogen stream of step (v) and/or the hydrogen feed of step (i) preferably are fresh hydrogen streams selected from the group consisting of hydrogen produced by steam reforming of natural gas, dissociation of hydrocarbons, and electrolysis. Most preferably, the hydrogen stream of step (v) and/or the hydrogen feed of step (i) are hydrogen from a wet hydrogen source which are produced in an aqueous electrolysis process.

By using a fresh hydrogen stream, and in a particular a wet hydrogen source, to strip the crude methanol, the process of WO2013/144041 is burdened by additional capital and operating expenditure or is required to be located adjacent an existing hydrogen source. We have found that by using a portion of the purge gas, the stripping efficiency of dissolved gases including carbon dioxide from the crude methanol may be maintained, the carbon dioxide requirement of the process reduced, and the methanol production capacity more readily enhanced.

Accordingly the invention provides a process for synthesising methanol comprising the steps of (i) passing a feed gas comprising a make-up gas containing hydrogen and carbon dioxide to a methanol synthesis loop, (ii) recovering a product gas mixture containing methanol from the methanol synthesis loop, (iii) cooling the product gas mixture to below the dew point to condense crude methanol, (iv) separating the crude methanol from an unreacted gas mixture, (v) passing a portion of the unreacted gas mixture to the methanol synthesis loop and (vi) recovering a portion of the unreacted gas mixture as a purge gas stream, characterised by contacting the crude methanol and a portion of the purge gas in a stripping unit to strip dissolved gases from the crude methanol thereby forming a stripped crude methanol and an enriched gas mixture, and feeding at least a portion of the enriched gas mixture to the methanol synthesis loop.

Methanol synthesis may be described by the following two equations:

$$3H_2 + CO_2 \leftrightarrows CH_3OH + H_2O$$

$$2H_2 + CO \leftrightarrows CH_3OH$$

There are two stoichiometric values that are commonly used to describe the proportions of the reactants fed to the methanol synthesis reactor. These are R and Z and may be determined from the molar concentrations of the components in the synthesis gas as follows;

$$R = ([H_2] - [CO_2])/([CO] + [CO_2])$$

$$Z = [H_2]/(2[CO] + 3[CO_2])$$

In addition, for methanol synthesis, it is often useful to determine a value S; being the sum of the $Nm^3/h$ of $H_2 + Nm^3/h$ of CO in the synthesis gas. S, Z and R may then be linked by the equation:

$$\text{Maximum methanol make } (Nm^3/h) = Z \cdot S/(R+1) \text{ for } Z \leq 1$$

$$\text{Maximum methanol make } (Nm^3/h) = S/(R+1) \text{ for } Z > 1$$

The ideal stoichiometric mixture arises when there is enough hydrogen to convert all of the carbon oxides into methanol. This is when R=2 and Z=1. However different synthesis gas generation techniques produce different synthesis gases having different proportions of the reactants.

Make-up gas, sometimes referred to as fresh synthesis gas, typically comprises hydrogen, carbon monoxide, and carbon dioxide, but in some processes, may consist of hydrogen and carbon dioxide or hydrogen and carbon monoxide.

Make-up gas in the present invention may be generated by any known method including processes including one or more steps of steam reforming, partial oxidation, autothermal reforming and gasification. However, the present invention is also of use in methanol synthesis processes that use reactive synthesis gases. By "reactive synthesis gases" we mean a synthesis gas comprising hydrogen, carbon monoxide and carbon dioxide in which the ratio (by volume) of carbon monoxide to carbon dioxide is typically 2:1, preferably 5:1. In the present process, the make-up gas is preferably one generated either by processes including the steam reforming and/or autothermal reforming of natural gas or by the gasification of coal or biomass.

In steam reforming processes, the make-up gas may be generated by steam reforming a hydrocarbon, such as natural gas, with steam and optionally carbon dioxide in a fired steam reformer, in which catalyst-filled tubes are externally heated by combusting a fuel gas with air, to form a synthesis gas comprising hydrogen, carbon monoxide and carbon dioxide. Alternatively, the make-up gas may be generated by combined reforming of a hydrocarbon, such as natural gas, by subjecting a first fraction of the hydrocarbon and steam to primary reforming in a primary steam reformer and secondary reforming a second fraction of the hydrocarbon, combined with the effluent of the primary reformer, with an oxygen-containing gas in an autothermal reformer. The latter has the advantage that the R-value may be controlled to about 2.0, but requires a source of oxygen-containing gas.

The make-up gas, before it is passed to the methanol synthesis loop, is typically cooled to condense steam, which is separated from the make-up gas using conventional condensate separation equipment. The condensate may be used to generate steam for the steam reforming. The make-up gas may then be compressed to the loop pressure using a syngas compressor and fed to the methanol synthesis loop.

It may be desirable to increase the carbon dioxide content of the feed gas, and thereby lower the R and Z values, by addition of a carbon dioxide gas stream to the make-up gas. Any source of carbon dioxide may be used. For example, the feed gas may comprise a carbon dioxide gas stream from the $CO_2$-recovery section of an ammonia plant or separated from a combustion flue gas. The flue gas may be from a boiler, a fired heater or a fired steam reformer. Carbon dioxide addition to the methanol synthesis loop normally would be expected to reduce the productivity of the methanol synthesis catalyst, requiring the catalyst volume to be increased. However, the Applicant has found that the combination of added carbon dioxide with the enriched gas mixture, which contains hydrogen, enhances the methanol production in the process without having to increase the catalyst volume.

The composition of feed gas mixture to the methanol synthesis loop is preferably; 10-20 mol % carbon monoxide, 0.5-10 mol % carbon dioxide, 55-85% hydrogen and the balance one or more inert gases. The R value of the feed gas (before enriched gas is added) is preferably 1.95-2.05 and Z is preferably 0.95-1.05.

Any methanol synthesis loop may be used. The methanol synthesis loop suitably comprises one or more methanol synthesis reactors, for example first, second and optionally third methanol synthesis reactors, each containing a bed of methanol synthesis catalyst, arranged in series and/or parallel that each produce product gas streams containing methanol. The methanol synthesis loop may therefore comprise one, two or more methanol synthesis reactors each containing a bed of methanol synthesis catalyst, and each fed with a feed gas comprising hydrogen and carbon dioxide, each producing a gas mixture containing methanol. A product gas mixture containing methanol is recovered from at least one methanol synthesis reactor. Methanol is recovered from one or more of the product gas mixtures. This may be achieved by cooling one or more of the methanol product gas streams to below the dew point, condensing methanol, and separating a crude liquid methanol product from the unreacted gases. Conventional heat exchange and gas-liquid separation equipment may be used. A particularly suitable heat exchange apparatus includes a gas-gas interchanger that uses a feed gas mixture for a methanol synthesis reactor to cool a methanol product gas stream from that reactor. The methanol product gas streams may be treated separately or may be combined before cooling and/or separating the crude liquid methanol product.

Separation of the crude liquid methanol product from one or more of the methanol product gas streams produces an unreacted gas mixture. A portion of the unreacted gas mixture is returned as a recycle or loop gas stream to one or more of the methanol synthesis reactors. Unreacted gas separated from a product gas mixture recovered from one methanol synthesis reactor may be returned to the same or a different methanol synthesis reactor. The unreacted gas mixture comprises hydrogen, carbon monoxide, and carbon dioxide and so may be used to generate additional methanol. The recycle gas stream may be recovered from at least one of one of the methanol product gas streams and recycled to at least one of the methanol synthesis reactors. If there is more than one recycle gas stream, these may be recycled separately to one or more of the methanol synthesis reactors or combined and fed to one or more of the methanol synthesis reactors.

The methanol synthesis reactor in the methanol synthesis loop may be an un-cooled adiabatic reactor. Alternatively, the methanol synthesis reactor may be cooled by heat exchange with a synthesis gas, such as in a quench reactor, or a reactor selected from a tube-cooled converter or a gas-cooled converter. Alternatively, the methanol synthesis reactor may be cooled by boiling water under pressure, such as in an axial-flow steam-raising converter, or a radial-flow steam-raising converter.

In an adiabatic reactor, the synthesis gas may pass axially, radially or axially and radially through a fixed bed of particulate methanol synthesis catalyst. The exothermic methanol synthesis reactions occur resulting in an increase in the temperature of the reacting gases. The inlet temperature to the bed therefore is desirably cooler than in cooled reactor systems to avoid over-heating of the catalyst which can be detrimental to selectivity and catalyst life. Alternatively, a cooled reactor may be used in which heat exchange with a coolant within the reactor may be used to minimise or control the temperature. A number of cooled reactor types exist that may be used. In one configuration, a fixed bed of particulate catalyst is cooled by tubes or plates through which a coolant heat exchange medium passes. In another configuration, the catalyst is disposed in tubes around which the coolant heat exchange medium passes. The methanol synthesis reactors may be cooled by the feed gas or by boiling water, typically under pressure. For example, the methanol synthesis reactor may be an axial steam raising converter, a radial-flow steam raising converter, a gas-cooled converter or a tube cooled converter.

In an axial-flow, steam-raising converter (aSRC), the synthesis gas typically passes axially through vertical, catalyst-containing tubes that are cooled in heat exchange with boiling water under pressure flowing outside the tubes. The catalyst may be provided in pelleted form directly in the tubes or may be provided in one or more cylindrical containers that direct the flow of synthesis gas both radially and axially to enhance heat transfer. Such contained catalysts and their use in methanol synthesis are described in U.S. Pat. No. 8,785,506. Steam raising converters in which the catalyst is present in tubes cooled by boiling water under pressure offer a particularly useful means to remove heat from the catalyst.

In a radial-flow steam raising converter (rSRC) the synthesis gas typically passes radially (inwards or outwards) through a bed of particulate catalyst which is cooled by a plurality of tubes or plates through boiling water under pressure is fed as coolant. Such reactors are known and are described for example in U.S. Pat. No. 4,321,234. They offer a lower pressure drop than an aSRC but have a more complicated internal construction.

In a tube-cooled converter, the catalyst bed is cooled by synthesis gas passing through tubes disposed within the bed that are open-ended and discharge the heated gas to the space above the catalyst within the reactor shell. The heated gas may then pass directly through the bed of catalyst without leaving the converter. TCC's can provide sufficient cooling area for a range of synthesis gas compositions and may be used under a wide range of conditions. As an alternative to a TCC, a gas-cooled converter (GCC) may be used to cool the catalyst bed by passing the synthesis gas though tubes or plates in a heat exchanger-type arrangement. In this case the heated synthesis gas is withdrawn from the converter before being returned back to the catalyst bed. An example of a GCC is described in U.S. Pat. No. 5,827,901.

Alternatively, the methanol synthesis reactor may be a quench reactor in which one or more fixed beds of particulate methanol synthesis catalyst are cooled by a synthesis gas mixture injected into the reactor within or between the beds. Such reactors are described, for example, in U.S. Pat. No. 4,411,877.

In a process comprising first and second methanol synthesis reactors, the first methanol synthesis reactor is preferably cooled by boiling water, such as in an axial-flow steam-raising converter or a radial-flow steam-raising converter, more preferably an axial-flow steam raising converter. The second methanol synthesis reactor may be a radial-flow steam-raising converter. Such arrangements are particularly useful in the present invention due to the characteristics and performance of these reactors with different feed gas mixtures. Alternatively, the second methanol may be cooled by a synthesis gas comprising hydrogen and carbon dioxide. Accordingly, the second methanol synthesis reactor may be a cooled reactor selected from a tube cooled converter (TCC) and a gas-cooled converter (GCC). A tube-cooled converter is preferred because of its simpler design. If a third methanol synthesis reactor is present, it is preferably cooled by boiling water. The third methanol synthesis reactor may then suitably be a steam-raising converter selected from an axial-flow steam-raising converter and a radial-flow steam-raising converter, most preferably an axial-flow steam raising converter. The first and second methanol synthesis reactors may be connected in series in which case the synthesis gas fed to the second methanol synthesis reactor comprises at least a portion of a methanol product gas stream recovered from the first methanol synthesis reactor. In such an arrangement, preferably the synthesis gas fed to the second methanol synthesis reactor comprises all of the methanol product gas stream recovered from the first methanol synthesis reactor. The methanol synthesis catalysts in each of the methanol synthesis reactors may be the same or different.

The methanol synthesis catalysts are preferably copper-containing methanol synthesis catalysts, which are commercially available. In particular, the methanol synthesis catalysts are one or more particulate copper/zinc oxide/alumina catalysts, which may comprise one or more promoters. Particularly suitable catalysts are Mg-promoted copper/zinc oxide/alumina catalysts as described in U.S. Pat. No. 4,788,175.

Methanol synthesis may be effected in the methanol synthesis reactors at pressures in the range 10 to 120 bar abs, and temperatures in the range 130° C. to 350° C. The pressures at the reactor inlets is preferably 50-100 bar abs, more preferably 70-90 bar abs. The temperature of the synthesis gas at the reactor inlets is preferably in the range 200-250° C. and at the outlets preferably in the range 230-280° C.

The portion of the unreacted gas mixture making up the recycle gas stream to the methanol synthesis will typically be at a lower pressure than the make-up gas and so preferably the recycle gas stream is compressed by one or more compressors or circulators. The resulting compressed recycle gas stream may be mixed with make-up gas or feed gas or enriched gas mixture to form the feed to the one or more methanol synthesis reactors in the methanol synthesis loop.

The recycle ratios to form the feed gas mixtures to the one or more methanol synthesis reactors may be in the range 0.5:1 to 5:1 preferably 1:1 to 3:1. By the term "recycle ratio", we mean the molar flow ratio of the recycled gas stream to the make-up gas that form the gas mixtures fed to the one or more methanol synthesis reactors.

A portion of the unreacted gas mixture separated from the crude liquid methanol is removed from the loop as the purge gas stream. The purge gas stream may be removed continuously or periodically to prevent the unwanted build-up of inert gases, such as nitrogen, argon and methane in the synthesis loop. The purge gas stream may be recovered from the separated unreacted gases before or after compression in the circulator. Purge gas streams, especially in processes using steam reforming as a source of the make-up gas, are hydrogen rich. The purge stream preferably contains 50-90% by volume of hydrogen and one or more of carbon monoxide, carbon dioxide, nitrogen, argon and methane.

A portion of the purge gas stream is used to strip or remove dissolved gases from the separated liquid crude methanol. The dissolved gases are suitably removed in a stripping unit comprising one or more stripping vessels to which a liquid crude methanol stream and a stripping gas are fed. The liquid crude methanol and a portion of the purge gas may be continuously fed to the stripping unit and contacted therein in a counter-current or co-current manner to remove the dissolved gases from the crude methanol. Alternatively, the liquid crude methanol may be sparged with the portion of the purge gas in the stripping unit. Suitably, the crude methanol and portion of the purge gas stream may be fed to an intermediate flash vessel located downstream of the gas-liquid separator and upstream of a purification unit, where they are contacted to remove the dissolved gases from the crude methanol and form the stripped crude methanol.

In the present invention, a portion of the purge gas is fed to the stripping unit. By "a portion of the purge gas" we include a portion of the purge gas itself or a gas obtained from the purge gas. Thus, in one arrangement, a portion of the purge gas stream itself comprising hydrogen and carbon oxides is used to strip the dissolved gases from the crude methanol. The portion used may be 10-90% by volume of the purge gas stream. The remaining portion is removed to reduce the build-up of inert gases in the loop. Whereas the portion of the purge gas stream may be fed directly to the stripping unit, it may be desirable to increase or decrease the hydrogen content of gas fed to the stripping unit. Thus, in another arrangement, at least a portion of the purge gas stream is separated into a hydrogen-rich gas stream and a hydrogen-depleted gas stream and at least a portion of the hydrogen-rich gas stream or the hydrogen depleted gas stream fed to the stripping unit. In this arrangement, preferably all of the purge gas is subjected to the separation step. Some or all of the hydrogen-rich gas or hydrogen depleted gas stream may be fed to the stripping unit. The separation of the hydrogen-rich and hydrogen-depleted gas streams may be practiced using known separation equipment such as hydrogen membrane separator or a pressure swing adsorption unit, or a cold box separation system. Using these techniques over 50% of the hydrogen present in the purge gas may be recovered. In a preferred arrangement, a hydrogen-rich gas stream is recovered from the purge gas and the hydrogen-rich gas stream used to strip the dissolved gases from the crude methanol.

Using the hydrogen-rich gas instead of the purge gas allows re-use of the separated carbon oxides and methane in the hydrogen-depleted gas stream in the make-up gas generation, and minimises the inert gases returned to the loop and so passed forward to the purification stage. The hydrogen-rich gas recovered from the purge gas stream desirably comprises >95% by volume of $H_2$.

The hydrogen-depleted gas, which will typically contain carbon oxides and methane, may be used as a fuel. For example, the hydrogen-depleted gas may be combusted to produce heat in a fired steam reformer. Alternatively, where the nitrogen and argon contents of the hydrogen-depleted gas are low, a portion of it may be fed to the synthesis gas generation step as a feed to form part of the make-up gas. However, preferably at least 50% vol. of the hydrogen-depleted gas is burned as fuel to control the build-up of inert gases. Where a membrane is used to separate the hydrogen-rich stream, the hydrogen-depleted stream will be at a pressure that enables it to be sent for use as part of the hydrocarbon feedstock for reforming without further compression. Where a pressure swing absorption system is used to separate the hydrogen-rich stream, the hydrogen-depleted stream will be at a low pressure, typically 2-5 bar abs, and so is better suited for use as a fuel gas.

The products from the stripping unit are a liquid stripped crude methanol and an enriched gas mixture containing hydrogen and gases that have been stripped from the crude methanol product. The stripped gases include carbon dioxide, which along with the hydrogen in the enriched gas mixture are returned to the methanol synthesis loop as a source of additional methanol. The enriched gas mixture may be added to the methanol synthesis loop at any point. For example, the enriched gas mixture may be combined with the make-up gas, before or after the addition of any carbon dioxide gas stream or may be added to a combination of the feed gas and the recycle gas stream in the loop. The enriched gas mixture may be added to the loop before or after compression, for example, it may be fed to the suction or interstage of the syngas compressor or directly to the loop. Where a hydrogen-rich stream provided by membrane separation from the purge gas stream is used as the stripping gas, the enriched gas mixture will typically be at a pressure that allows it to be combined with the make-up gas at the suction of the syngas compressor. Where a hydrogen-rich stream provided by pressure swing absorption from the purge gas stream is used as the stripping gas, and the purge gas is recovered before compression in the circulator, the enriched gas mixture may suitably be fed to the interstage of the syngas compressor. Where a hydrogen-rich stream provided by pressure swing absorption from the purge gas stream is used as the stripping gas, and the purge gas is recovered after compression in the circulator, the enriched gas mixture may suitably be added to the methanol synthesis loop, e.g. at the suction of the circulator. Alternatively, if desired, the hydrogen-rich gas stream may be compressed in a separate compressor to enable its direct addition to the methanol synthesis loop.

The purge gas stream or the enriched gas mixture may contain methanol and so, if desired, additional methanol may be recovered from the purge gas stream or the enriched gas mixture using a water wash, and the recovered methanol and water sent for purification with the stripped crude methanol.

The stripped crude methanol stream recovered from the methanol production unit contains water, along with small amounts of higher alcohols and other impurities. The stripped crude methanol may be subjected to one or more purification stages including one or more, preferably two or three, stages of distillation in a methanol purification unit comprising one, two or more distillation columns. The de-gassing stage and distillation stages may be heated using heat recovered from the process, for example in the cooling of a product gas stream, or other sources. Preferably at least a portion of the crude methanol is purified by distillation to produce a purified methanol product.

The purified methanol product may be subjected to further processing, for example to produce derivatives such as dimethyl ether or formaldehyde. Alternatively, the methanol may be used as a fuel.

The invention will be further described by reference to the figures in which.

It will be understood by those skilled in the art that the drawings are diagrammatic and that further items of equipment such as feedstock drums, pumps, vacuum pumps, compressors, gas recycling compressors, temperature sensors, pressure sensors, pressure relief valves, control valves, flow controllers, level controllers, holding tanks, storage tanks and the like may be required in a commercial plant. Provision of such ancillary equipment forms no part of the present invention and is in accordance with conventional chemical engineering practice.

Figure 1:
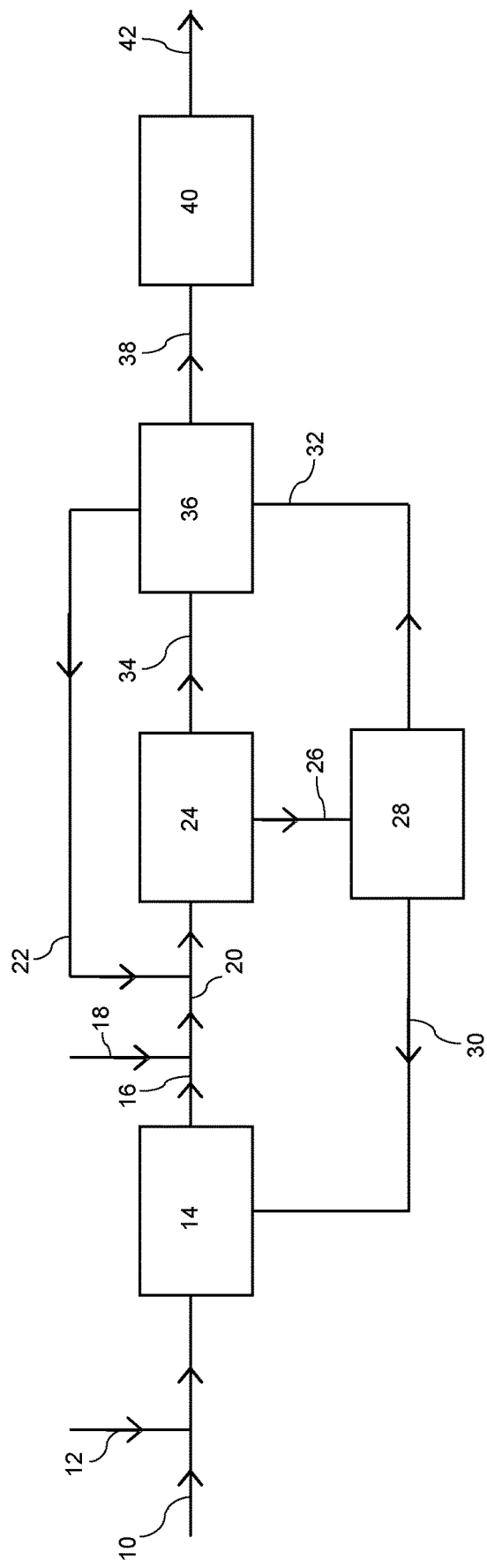
FIG. 1 depicts a process according to a first embodiment of the invention.

In FIG. 1, a natural gas stream 10 is mixed with steam from line 12 and the resulting mixture fed to a synthesis gas generation unit 14 comprising a fired steam reformer where it is catalytically reformed to form a synthesis gas stream comprising hydrogen, carbon monoxide and carbon dioxide. The synthesis gas stream is cooled and de-watered in heat exchange and separation equipment (not shown) to produce a make-up gas, which is recovered from the synthesis gas generation unit 14 via a line 16.

The make-up gas 16 is mixed with a carbon dioxide stream provided by line 18 to form a feed gas 20. The composition of the feed gas 20 may be used to determine the R-value of the external feeds to the methanol synthesis loop. An enriched gas mixture from line 22 is combined with the feed gas 20 and the resulting enriched feed gas compressed in a syngas compressor (not shown) and fed to a methanol synthesis unit 24. The methanol synthesis unit comprises a methanol synthesis loop in which the feed gas is mixed with a recycled stream of unreacted gas comprising hydrogen, carbon dioxide and carbon monoxide and fed to one, two or more methanol synthesis reactors, each containing a methanol synthesis catalyst, operating in series or parallel to generate a product gas stream containing methanol. The product gas stream is cooled to condense and separate a liquid crude methanol from unreacted gas, a portion of which is compressed in a circulator and recycled to the methanol synthesis reactor.

A portion of the unreacted gas is withdrawn as a purge gas stream upstream of the circulator and passed from the methanol synthesis unit 24 via line 26 to a hydrogen separation unit 28 in which the purge gas stream is separated into a hydrogen-rich stream and a hydrogen-depleted stream by passing the purge gas stream through a membrane. The hydrogen depleted stream is fed by line 30 from the separation unit 28 to the syngas generation unit 14 to be combusted as a fuel, e.g. in the fired steam reformer.

The hydrogen-rich gas stream, fed by line 32 from the separation unit 28, and the crude methanol fed by line 34 from the methanol synthesis unit 24, are passed to a methanol stripping unit 36. In the methanol stripping unit 36, the crude methanol and the hydrogen-rich gas stream are contacted and the dissolved gases in the crude methanol are released into the hydrogen-rich gas to form and enriched gas mixture and a stripped crude methanol product. The enriched gas mixture is fed from the stripping unit 36 via line 22 to the suction or interstage of the syngas compressor (not shown) to form an enriched feed gas to the methanol synthesis unit 24. The stripped crude methanol is fed via line 38 from the stripping unit to a purification unit 40 comprising one, two or more distillation columns to produce a purified methanol product recovered via line 42.

Figure 2:
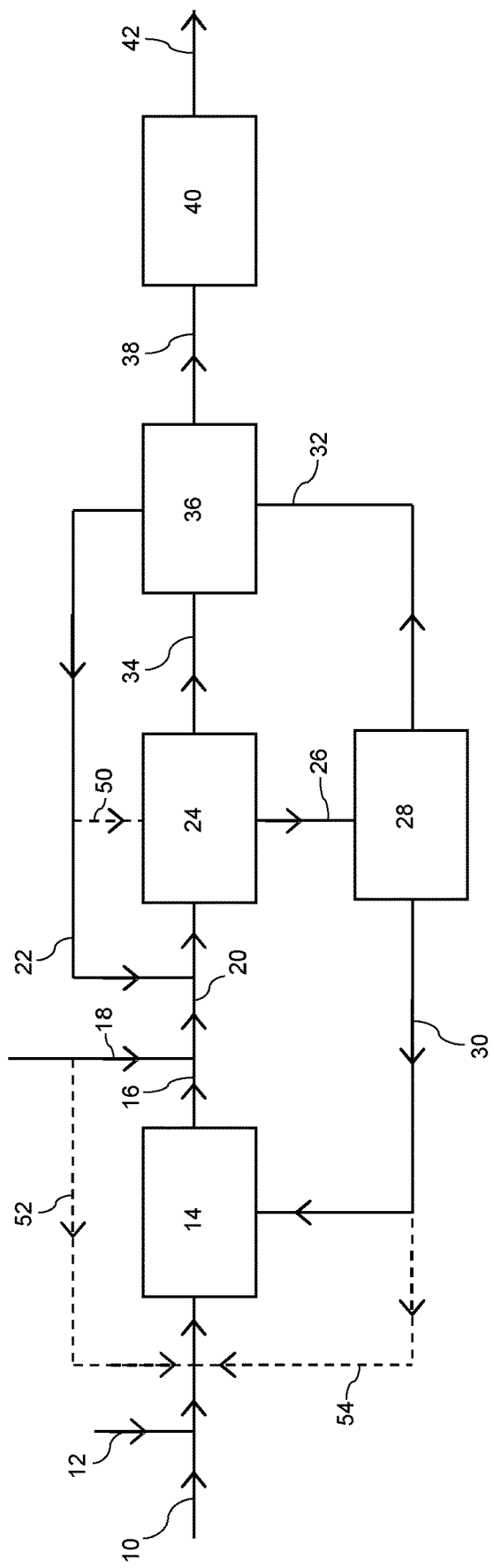
FIG. 2 depicts the process according to FIG. 1 with additional or alternative features.

In FIG. 2, the process if FIG. 1 is depicted with a number of alternatives that may be used separately or in combination with each other.

As an alternative to combining the enriched gas mixture 22 from the stripping unit 36 with the make-up gas, the enriched gas mixture 22 may be fed from the stripping unit 36 directly to the methanol synthesis loop via line 50, (shown as a dotted line). If the stripping unit is at a lower pressure than the loop then a compressor will be required in line 50. However, by taking the purge gas stream from downstream of the circulator and using a high pressure separation technique, such as pressure-swing adsorption, the enriched gas mixture will be at a pressure high enough that it can be fed to the loop upstream of the circulator without the need for further compression.

As an alternative to combining the carbon dioxide provided by line 18 with the make-up gas 16, at least a portion of the carbon dioxide stream may be combined with the hydrocarbon-containing feed to the synthesis gas generation unit 14, via line 52, (shown as a dotted line).

As an alternative to feeding the hydrogen-depleted gas from the separation unit 28 as fuel in the synthesis gas generation unit 14 via line 30, a portion of the hydrogen depleted gas may be combined with the hydrocarbon-containing feed to the synthesis gas generation unit 14, via line 54, (shown as a dotted line).

As an alternative to simply using just a fired steam reformer in the syngas generation unit 14, the syngas generation is by combined reforming. Thus, the syngas generation unit 14 comprises a combination of a fired steam reformer and an oxygen-fed autothermal reformer, with a portion of the natural gas feed and the primary reformer effluent fed to the autothermal reformer to generate a crude synthesis gas. The crude synthesis gas is cooled and the condensate separated to generate the make-up gas as before.

As an alternative to simply using just a fired steam reformer in the syngas generation unit 14, the syngas generation is by gasification of a carbonaceous feedstock, alone or in combination with one or more stages of steam reforming in parallel or series.

The invention will be further described by reference to the following examples.

EXAMPLE 1

Examples A-D were based on a process using a single fired steam reformer fed with natural gas and steam that produced make-up gas with S=300,000 Nm$^3$/h at about 20 bar abs pressure. The R-value of the make-up gas exit the steam reformer was 2.96. The make-up gas and other gases were fed to a methanol synthesis loop comprising a single methanol synthesis reactor based on a radial-flow-steam-raising converter design as described in U.S. Pat. No. 4,321,234 containing a standard copper catalyst. In each case the R-value of the gas at the inlet of the methanol synthesis converter was 5.00. The methanol converter exit pressure was at 80 bar abs. The methanol recovery processes were the same in each case. The theoretical maximum methanol make from S=300,000 Nm$^3$/h is 100,000 Nm$^3$/h.

Examples A, B and C are Comparative Examples and have no addition of an enriched gas from a stripping unit to the methanol synthesis loop.

Comparative Example A: Carbon dioxide addition to the loop. A carbon dioxide stream was added to the make-up gas to get to R=2.09. Subsequent addition of the recycle gas stream gave R=5.00 at the inlet of the methanol synthesis converter. The process made 88,557 Nm$^3$/h of methanol, which is a syngas efficiency of 88.56%.

Comparative Example B: Carbon dioxide and purge gas hydrogen addition to the loop. A carbon dioxide stream was added to the make-up gas to get to R=2.00 before the addition of a hydrogen-rich gas extracted from the purge gas. Subsequent addition of the recycle gas stream gave R=5.00 at the inlet of the methanol synthesis converter. The hydrogen-rich gas was not used to strip dissolved gases from the crude methanol. The process made 91,948 Nm$^3$/h of methanol, which is a syngas efficiency of 91.95%. This Example demonstrates that, for the same R-value at the inlet of the methanol converter, the syngas efficiency has improved by 3.4% compared to Example A.

Comparative Example C: Carbon dioxide and purge gas hydrogen addition to the loop. The process of comparative Example B was repeated but with 70% (by mole) of the hydrogen in the purge gas recycled. A carbon dioxide stream was added to the make-up gas to get to R=1.93 before addition of the hydrogen rich gas extracted from the purge gas. Subsequent addition of the recycle gas stream gave R=5.00 at the inlet of the methanol synthesis converter. The process made 94,767 Nm$^3$/h of methanol, which is a syngas efficiency of 94.77%. This Example demonstrates that, for the same R-value at the inlet of the methanol converter, adding more hydrogen and carbon dioxide improves the syngas efficiency.

Example D according to the invention as depicted in FIG. 1: Carbon dioxide and enriched gas addition to the loop. The process of comparative Example C was repeated but with stripping of the crude methanol using the hydrogen rich gas, and addition of the resulting enriched gas to the make-up gas. A carbon dioxide stream was added to the make-up gas to get to R=2.00 before addition of the enriched gas stream from the stripping unit. Subsequent addition of the recycle gas stream gave R=5.00 at the inlet of the methanol synthesis converter. The process made 94,483 Nm$^3$/h of methanol, which is a syngas efficiency of 94.48%. Whereas the syngas efficiency is no higher than Comparative Example C, compared to comparative Example C the process used 2,557 Nm$^3$/h less carbon dioxide.

The number of kilograms of carbon dioxide that is needed to make each extra kilogram of methanol, above the production in Example A, is almost the same for Examples B and C, at 1.23 and 1.24 respectively. The inclusion of the stripping stage in Example D therefore reduced the carbon dioxide consumption to 0.71 kg of carbon dioxide for each extra kilogram of methanol. This is a significant reduction in the marginal consumption of carbon dioxide. There is both an operating cost (in terms of increase energy consumption) and a capital cost for the equipment needed for recovery of carbon dioxide. By stripping the crude methanol to recover carbon dioxide and other dissolved gases back to the process, then there is a saving in the size for recovery of carbon dioxide from the flue gas along with an associated saving in operating cost.

In both Example C and Example D, approximately 70% (by mole) of the hydrogen available in the purge gas was recovered into the hydrogen-rich gas stream. A modern membrane-based hydrogen recovery system can achieve a hydrogen recovery around 95%. With such a high hydrogen recovery, there is no disincentive to operate at R-values at the inlet of the methanol synthesis reactor of 5.00 or higher. Higher R-values than 5.00 would enable the efficiency of Example D to be increased further to supersede that in Example C. The methanol synthesis reactor used in these calculations was a radial-flow, steam-raising converter. The advantage of an R-value 5.0 at the inlet of the radial-flow steam-raising converter is that the same synthesis catalyst volume for Example A will produce over 6% more methanol when used in the arrangement of this invention.

Almost identical benefits are found when some or all of the carbon dioxide was added to the natural gas/steam feed upstream of the fired steam reformer instead of to the make-up gas.

It is also possible to further enhance the process by recycle of the hydrogen-depleted stream as feedstock to the fired steam reformer. Due to the low nitrogen content of the natural gas used, it is possible to recycle a large fraction of the hydrogen-depleted stream. A study of the methanol synthesis reactor inlet stream showed that the main inert gas in the methanol synthesis loop was methane and not nitrogen, so the recycle of a large fraction of the hydrogen-depleted stream had a minor impact on the syngas efficiency.

The results are set out in the tables below.

|  | Comparative Examples | | | Example |
|---|---|---|---|---|
|  | A | B | C | D |
| S ($H_2$ + CO) ($Nm^3/h$) | 300000 | 300000 | 300000 | 300000 |
| Methanol in the stripped crude product ($Nm^3/h$) | 88557 | 91948 | 94767 | 94483 |
| Syngas Efficiency | 88.56% | 91.95% | 94.77% | 94.48% |
| R-value of make-up gas | 2.96 | 2.96 | 2.96 | 2.96 |
| R-value make-up gas with $CO_2$ addition | 2.09 | 2.00 | 1.93 | 2.00 |
| R-value make-up gas with $CO_2$ and hydrogen stream addition | 2.09 | 2.11 | 2.13 | 2.15 |
| R-value inlet methanol synthesis reactor including recycle stream | 5.00 | 5.00 | 5.00 | 5.00 |
| kg of $CO_2$ to make one extra kg of methanol |  | 1.23 | 1.24 | 0.71 |

| Stream | Component ($Nm^3/h$) | Comparative Examples | | | Example |
|---|---|---|---|---|---|
|  |  | A | B | C | D |
| Make-up Gas 16 | $H_2O$ | 1514 | 1514 | 1514 | 1514 |
|  | $CH_3OH$ | 0 | 0 | 0 | 0 |
|  | CO | 50780 | 50780 | 50780 | 50780 |
|  | $CO_2$ | 24922 | 24922 | 24922 | 24922 |
|  | $H_2$ | 249220 | 249220 | 249220 | 249220 |
|  | $CH_4$ | 10448 | 10448 | 10448 | 10448 |
|  | $N_2$ | 264 | 264 | 264 | 264 |
| Import $CO_2$ 18 | $H_2O$ | 93 | 106 | 118 | 106 |
|  | $CO_2$ | 21256 | 24299 | 26855 | 24298 |
| Hydrogen-rich gas 32 | $H_2O$ | 0 | 19 | 35 | 38 |
|  | $CH_3OH$ | 0 | 20 | 36 | 39 |
|  | CO | 0 | 65 | 119 | 128 |
|  | $CO_2$ | 0 | 1529 | 2899 | 3112 |
|  | $H_2$ | 0 | 16302 | 30574 | 32853 |
|  | $CH_4$ | 0 | 408 | 689 | 754 |
|  | $N_2$ | 0 | 6 | 10 | 10 |
| Hydrogen-rich gas to the loop | $H_2O$ | 0 | 19 | 35 | 38 |
|  | $CH_3OH$ | 0 | 20 | 36 | 39 |
|  | CO | 0 | 65 | 119 | 223 |
|  | $CO_2$ | 0 | 1529 | 2899 | 5629 |
|  | $H_2$ | 0 | 16302 | 30574 | 33102 |
|  | $CH_4$ | 0 | 408 | 689 | 1676 |
|  | $N_2$ | 0 | 6 | 10 | 18 |
| Make-up gas + CO2 | $H_2O$ | 1608 | 1621 | 1632 | 1621 |
|  | CO | 50778 | 50779 | 50780 | 50780 |
|  | $CO_2$ | 46178 | 49221 | 51777 | 49220 |
|  | $H_2$ | 249222 | 249221 | 249220 | 249220 |
|  | $CH_4$ | 10447 | 10448 | 10449 | 10448 |
|  | $N_2$ | 268 | 266 | 264 | 264 |
| Methanol converter inlet | $H_2O$ | 41903 | 45555 | 48621 | 48441 |
|  | $CH_3OH$ | 97374 | 100569 | 103243 | 103000 |
|  | CO | 63657 | 63021 | 62598 | 62759 |
|  | $CO_2$ | 134076 | 140152 | 145116 | 144969 |
|  | $H_2$ | 1122812 | 1156105 | 1183678 | 1183553 |
|  | $CH_4$ | 336555 | 306635 | 282545 | 287708 |
|  | $N_2$ | 9231 | 8182 | 7342 | 7053 |

EXAMPLE 2

Examples E-H were similar to the examples A-D but used combined reforming of the natural gas using a fired steam-methane reformer (SMR) and an autothermal reformer (ATR) in place of the fired steam reformer and so were performed without imported $CO_2$ addition to the make-up gas. The combined reforming produced make up gas with S=300,000 $Nm^3/h$ at about 35 bar abs pressure. The methanol loop and recovery were the same as in Example 1.

Comparative Example E: 41.6% of the natural gas was bypassed around the SMR and 48,308 $Nm^3/h$ of oxygen was used in the ATR to provide a make-up gas with R=2.003. Subsequent addition of the recycle gas stream gave R=5.00 at the inlet of the methanol synthesis converter. The process made 97,282 $Nm^3/h$ of methanol, which is a syngas efficiency of 97.28%. This example shows the benefit of using a reactive synthesis gas such as that formed by combined reforming to the overall syngas efficiency.

Comparative Example F: Purge gas hydrogen addition to the loop. 42.6% of the natural gas was bypassed around the SMR and 48,512 $Nm^3/h$ of oxygen was used in the ATR. The make-up gas had R=2.004, before addition of the hydrogen-rich gas extracted from the purge gas. Subsequent addition of the recycle gas stream gave R=5.00 at the inlet of the methanol synthesis converter. The process made 97,400 $Nm^3/h$ of methanol, which is a syngas efficiency of 97.40%. The recycle of hydrogen-rich gas is very small for this example, so the change in syngas efficiency compared to Example E is also very small.

Comparative Example G: Purge gas hydrogen addition to the loop. The process of comparative Example F was repeated but with 70% (by mole) of the hydrogen in the purge gas recycled. 43.3% of the natural gas was bypassed around the SMR and 50,521 $Nm^3/h$ of oxygen is used in the ATR. The make-up gas had R=1.97 before addition of the hydrogen rich gas extracted from the purge gas. Subsequent addition of the recycle gas stream gave R=5.00 at the inlet of the methanol synthesis converter. The process made 98,553 $Nm^3/h$ of methanol, which is a syngas efficiency of 98.55%.

Example H according to the invention: Enriched gas addition to the loop. The process of comparative Example G was repeated but with stripping of the crude methanol with the hydrogen rich gas and addition of the resulting enriched gas to the make-up gas. 50.2% of the natural gas is bypassed around the SMR and 48,038 $Nm^3/h$ of oxygen is used in the ATR. The make-up gas had R=2.007 before addition of the enriched gas stream from the stripping unit. Subsequent addition of the recycle gas stream gave R=5.00 at the inlet of the methanol synthesis converter. The process made 98,376 $Nm^3/h$ of methanol, which is a syngas efficiency of 98.38%.

The number of kilograms of $O_2$ that is needed to make each extra kilogram of methanol, above the production in Example E, is almost the same for Examples F and G, at 1.72 and 1.74 respectively. The inclusion of the stripping stage reduced the $O_2$ consumption by 0.25 kg of $O_2$ for each extra kilogram of methanol. This is a significant reduction in the marginal consumption of $O_2$.

The syngas efficiency for Example H is only slightly lower than for Example G, but the cost of oxygen on most projects means that the economics (both capital cost and operating cost) of the lower oxygen consumption for example H will be preferred in most situations.

The results are set out in the tables below.

|  | Comparative Examples | | | Example |
|---|---|---|---|---|
|  | E | F | G | H |
| Bypass around the SMR (mole %) | 41.6 | 42.6 | 43.3 | 50.2 |
| S ($H_2$ + CO) (Nm3/h) | 300000 | 300000 | 300000 | 300000 |
| Methanol in the stripped crude product (Nm3/h) | 97282 | 97400 | 98553 | 98376 |
| Syngas Efficiency | 97.28% | 97.40% | 98.55% | 98.38% |
| R-value of make-up gas | 2.003 | 2.000 | 1.970 | 2.007 |
| R-value of combined feeds to loop | 2.003 | 2.004 | 2.014 | 2.023 |
| R-value inlet methanol synthesis reactor | 5.00 | 5.00 | 5.00 | 5.00 |
| kg of $O_2$ to make one extra kg of methanol |  | 1.72 | 1.74 | −0.25 |

| Stream | Component (Nm³/h) | Comparative Examples | | | Example |
|---|---|---|---|---|---|
|  |  | E | F | G | H |
| Make-up Gas 16 | $H_2O$ | 1481 | 1480 | 1477 | 1481 |
|  | $CH_3OH$ | 0 | 0 | 0 | 0 |
|  | CO | 76708 | 76939 | 79240 | 76407 |
|  | $CO_2$ | 23188 | 23061 | 21775 | 23354 |
|  | $H_2$ | 223292 | 223061 | 220760 | 223593 |
|  | $CH_4$ | 4132 | 4194 | 4870 | 4053 |
|  | $N_2$ + Ar | 797 | 795 | 779 | 724 |
| Import $O_2$ | Ar | 243 | 244 | 254 | 241 |
|  | $O_2$ | 48308 | 48512 | 50521 | 48038 |
| Hydrogen-rich gas 32 | $H_2O$ | 0 | 0 | 4 | 6 |
|  | $CH_3OH$ | 0 | 5 | 60 | 69 |
|  | CO | 0 | 34 | 389 | 452 |
|  | $CO_2$ | 0 | 35 | 380 | 494 |
|  | $H_2$ | 0 | 509 | 5603 | 6909 |
|  | $CH_4$ | 0 | 196 | 2330 | 2686 |
|  | $N_2$ + Ar | 0 | 48 | 458 | 479 |
| Hydrogen-rich gas to the loop | $H_2O$ | 0 | 0 | 4 | 6 |
|  | $CH_3OH$ | 0 | 1 | 9 | 11 |
|  | CO | 0 | 2 | 27 | 129 |

-continued

| | | Comparative Examples | | | Example |
|---|---|---|---|---|---|
| Stream | Component (Nm$^3$/h) | E | F | G | H |
| | $CO_2$ | 0 | 27 | 285 | 1665 |
| | $H_2$ | 0 | 484 | 5323 | 6840 |
| | $CH_4$ | 0 | 18 | 210 | 1499 |
| | $N_2$ + Ar | 0 | 1 | 13 | 88 |
| Methanol converter inlet | $H_2O$ | 1697 | 1696 | 1685 | 1753 |
| | $CH_3OH$ | 12599 | 12641 | 13080 | 12424 |
| | CO | 158969 | 159469 | 164570 | 157330 |
| | $CO_2$ | 108446 | 108180 | 105391 | 113237 |
| | $H_2$ | 1445518 | 1446421 | 1455177 | 1465485 |
| | $CH_4$ | 471835 | 475899 | 516223 | 485659 |
| | $N_2$ + Ar | 118469 | 116782 | 101358 | 86449 |

The invention claimed is:

1. A process for synthesising methanol comprising the steps of (i) passing a feed gas comprising a make-up gas containing hydrogen and carbon dioxide to a methanol synthesis loop, (ii) recovering a product gas mixture containing methanol from the methanol synthesis loop, (iii) cooling the product gas mixture to below the dew point to condense crude methanol, (iv) separating the crude methanol from an unreacted gas mixture, (v) passing a portion of the unreacted gas mixture to the methanol synthesis loop and (vi) recovering a portion of the unreacted gas mixture as a purge gas stream, characterised by contacting the crude methanol and a portion of the purge gas in a stripping unit to strip dissolved gases from the crude methanol thereby forming a stripped crude methanol and an enriched gas mixture, and feeding at least a portion of the enriched gas mixture to the methanol synthesis loop.

2. The process according to claim 1, wherein the make-up gas is generated by one or more steps of steam reforming, partial oxidation, autothermal reforming or gasification.

3. The process according to claim 1, wherein the make-up gas is generated by catalytic steam reforming a hydrocarbon with steam and optionally carbon dioxide in a fired steam reformer, or by combined reforming of a hydrocarbon by subjecting a first fraction of the hydrocarbon and steam to primary reforming in a primary steam reformer and secondary reforming a second fraction of the hydrocarbon, combined with the effluent of the primary reformer, with an oxygen-containing gas in an autothermal reformer.

4. The process according to claim 1, wherein a carbon dioxide gas stream is added to the make-up gas.

5. The process according to claim 1, wherein the crude methanol and a portion of the purge gas are fed to the stripping unit and contacted therein in a counter-current or co-current manner, or wherein the crude methanol is sparged with the portion of the purge gas.

6. The process according to claim 1, wherein at least a portion of the purge gas is separated into a hydrogen-rich gas stream and a hydrogen-depleted gas stream and at least a portion of the hydrogen-rich gas stream is fed to the stripping unit.

7. The process according to claim 6, wherein the hydrogen-depleted gas stream is used as a fuel, or is fed to the synthesis gas generation step to form part of the make-up gas.

8. The process according to claim 1, wherein the methanol synthesis loop comprises one, two or more methanol synthesis reactors each containing a bed of methanol synthesis catalyst, wherein the product gas mixture is recovered from at least one methanol synthesis reactor.

9. The process according to claim 1, wherein the methanol synthesis loop comprises one, two or more methanol synthesis reactors, each fed with a feed gas comprising hydrogen and carbon dioxide, each producing a product gas mixture, wherein an unreacted gas mixture separated from a product gas mixture recovered from one methanol synthesis reactor may be returned to the same or a different methanol synthesis reactor.

10. The process according to claim 8, wherein the methanol synthesis reactors are cooled by a synthesis gas or by boiling water.

11. The process according to claim 8, wherein the methanol synthesis catalyst is a copper-containing methanol synthesis catalyst.

12. The process according to claim 8, wherein methanol synthesis is effected in the methanol synthesis reactors at pressures in the range 10 to 120 bar abs, and temperatures in the range of 130° C. to 350° C.

13. The process according to claim 1, wherein the stripped crude methanol is subjected to one or more steps of distillation to produce a purified methanol product.

* * * * *